United States Patent
Malphurs

(10) Patent No.: US 11,173,669 B2
(45) Date of Patent: Nov. 16, 2021

(54) METHOD OF JOINING STRUCTURES MADE OF INCOMPATIBLE POLYMERS

(71) Applicant: Optical Integrity, Inc., Panama City Beach, FL (US)

(72) Inventor: Daniel Malphurs, Panama City Beach, FL (US)

(73) Assignee: OPTICAL INTEGRITY, INC., Panama City Beach, FL (US)

( * ) Notice: Subject to any disclaimer, the term of this patent is extended or adjusted under 35 U.S.C. 154(b) by 102 days.

(21) Appl. No.: 16/456,688

(22) Filed: Jun. 28, 2019

(65) Prior Publication Data
US 2020/0070427 A1 Mar. 5, 2020

Related U.S. Application Data

(60) Provisional application No. 62/691,744, filed on Jun. 29, 2018.

(51) Int. Cl.
*B29C 65/02* (2006.01)
*A61B 18/22* (2006.01)
(Continued)

(52) U.S. Cl.
CPC .......... *B29C 65/02* (2013.01); *A61B 18/22* (2013.01); *B29C 66/71* (2013.01);
(Continued)

(58) Field of Classification Search
CPC ... B29C 65/02; B29C 66/534; B29C 66/5261; B29C 65/565; B29C 66/712;
(Continued)

(56) References Cited

U.S. PATENT DOCUMENTS

| 6,282,349 B1 | 8/2001 | Griffin | |
| 2009/0287200 A1* | 11/2009 | Hanley | A61B 18/22 606/15 |
| 2019/0083177 A1* | 3/2019 | Brown | A61B 18/22 |

FOREIGN PATENT DOCUMENTS

WO WO2017-192869 A1 11/2017

\* cited by examiner

*Primary Examiner* — Vishal I Patel
(74) *Attorney, Agent, or Firm* — Bacon & Thomas, PLLC

(57) ABSTRACT

A first structure made of a first polymer is joined to a second structure made of an incompatible second polymer by the steps of welding small bands of compatible tubing or material to the first structure to create raised structures or ribs, and mechanically linking the second structure with the ribs or raised structures at the desired attachment point. The mechanical linkage may be accomplished by using heat shrinking or mechanical compression (such as crimping) to force the incompatible second polymer around the ribs or raised structures or, in the case of raised structures formed as threads or nubs, by inter-engagement between the threads or nubs on the first structure and corresponding structures, such as internal threading, nub-receiving slots, or internal surfaces, of the second structure. The option of using the welded raised structures as threads or nubs for a threaded, bayonet, pin-and-slot, snap-fit, or similar connection enables the second structure to be removed from the first structure and replaced whenever the second structure becomes worn during use. The first structure may be an surgical laser fiber with an ETFE buffer layer, and the second structure is a protective structure may be made of PTFE, PET, FEP or PFA.

7 Claims, 1 Drawing Sheet

(51) Int. Cl.
*B29C 65/00* (2006.01)
*B29K 67/00* (2006.01)
*B29K 27/18* (2006.01)

(52) U.S. Cl.
CPC ... *A61B 2018/2222* (2013.01); *B29K 2027/18* (2013.01); *B29K 2067/003* (2013.01)

(58) Field of Classification Search
CPC ..... B29C 65/68; B29C 66/71; B29C 66/1122; B29C 65/58; B29C 66/02; B29C 65/76; B29C 66/81471; B29C 66/73921; B29C 65/561; B29C 66/526; B29K 2027/18; B29K 2067/003; B29K 2023/08; B29K 2027/12; A61B 2018/2222; A61B 18/22

See application file for complete search history.

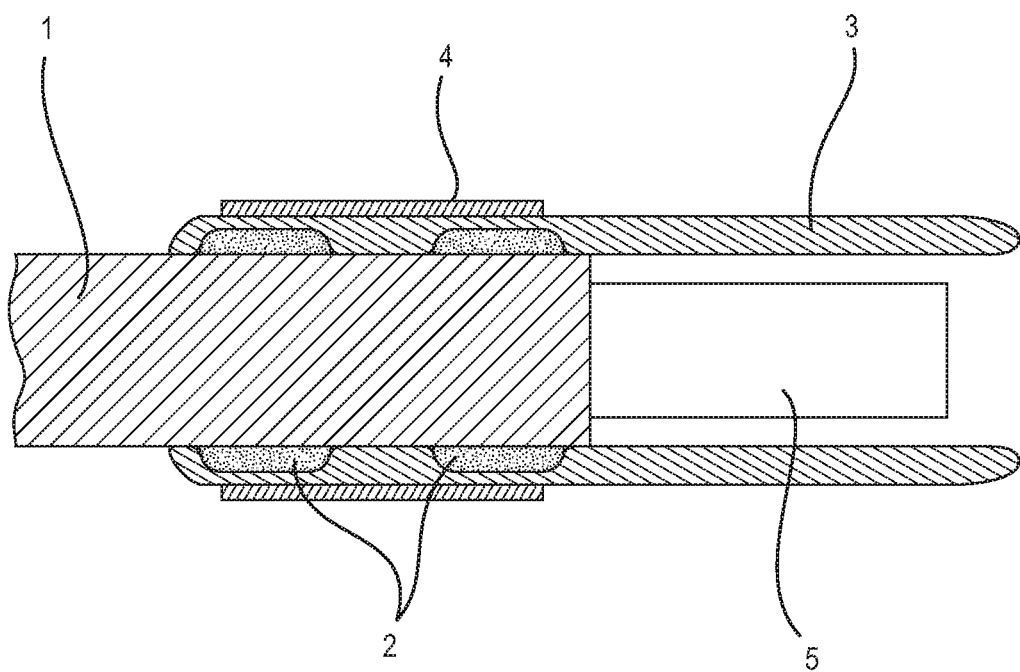

METHOD OF JOINING STRUCTURES MADE OF INCOMPATIBLE POLYMERS

BACKGROUND OF THE INVENTION

1. Field of the Invention

The invention relates to a method of joining incompatible polymers.

The method of the invention may be used, by way of example and not limitation, to attach a PTFE, PET, FEP, or PFA fiber tip protective structure to an ETFE buffer of a surgical laser fiber.

The invention also relates to a product made by the method of the invention, and to an arrangement for removably coupling a protective tip to an surgical laser fiber.

2. Description of Related Art

Some polymers will not chemically bond to each other and cannot be welded. For example, the fiber buffer of a surgical laser optical fiber is often made of ethylene tetrafluoroethylene (ETFE), while fiber tip protective structures such as the ones disclosed in the inventor's PCT Publication No. WO 2017/192869 and Provisional Patent Appl. Ser. No. 62/648,108, filed Mar. 26, 2018, and incorporated herein by reference, may be made of a soft polymer such as polytetrafluoroethylene (PTFE), polyethylene terephthalate (PET), fluorinated ethylene propylene (FEP), or perfluoroalkoxy alkanes (PFA). As a result, attachment of soft fiber tip protective structures to fibers having ETFE buffer layers by welding or chemical bonding is currently considered to be impractical from standpoints of manufacturing efficiency and cost.

Alternatives to welding and chemical bonding include use of adhesives and mechanical attachment means. However, each alternative method has disadvantages in terms of safety and performance of the finished product.

U.S. Pat. No. 6,282,349 (Griffin) includes a detailed discussion of the disadvantages of using adhesives to attach a quartz ferrule to a fiber, including contamination by the outgassing adhesive of the laser output lens and the possibility of sudden, explosive failure of the fiber termination as well as low yield if the viscosity of the adhesive is increased to avoid outgassing or the ferrule is countersunk to move the adhesive away from the end of the fiber. In addition, the Griffin patent discusses the disadvantages of crimping the ferrule directly to the fiber, including lowered connector mass and incompatibility with surgical laser interlocks. These disadvantages also apply to attachment of polymeric protective structures rather than quartz ferrules, but Griffin's solution of crimping the fiber into a cylindrical beam block extension is suitable only for rigid structures such as a quartz ferrule, and not for attachment of soft polymer protective structures such as the ones disclosed in PCT Publication No. WO 2017/192869 and Provisional Patent Appl. Ser. No. 62/648,108.

SUMMARY OF THE INVENTION

It is an objective of the invention to provide a method of joining structures made of incompatible polymers.

It is a further objective of the invention provide a method of attaching a fiber tip protective structure to a surgical laser fiber having a polymeric outer layer that is incompatible with a polymeric material of the fiber tip protective structure.

It is a still further objective of the invention to provide a method of attaching a PTFE, PET, FEP, or PFA fiber tip protective structure to an ETFE buffer of a surgical laser fiber.

It is also an objective of the invention to provide products made of incompatible polymers that have been joined together by the method of the invention.

It is yet another objective of the invention to provide an arrangement for removably coupling a protective tip to an surgical laser fiber.

Although the preferred embodiments of the invention are directed to fiber tip protective structures, it will be appreciated by those skilled in the art that the method of the invention may be applied to joining of incompatible polymers in contexts other than surgical laser fiber tip protection.

Furthermore, although specific incompatible polymers are described herein, it is will be appreciated by those skilled in the art that the method of the invention may be applied to incompatible polymers other than PTFE, PET, FEP, PFA, and/or ETFE According to a preferred embodiment of the invention, joining of a first structure made of a first polymer to a second structure made of an incompatible second polymer is accomplished by the steps of:
a. welding small bands of compatible tubing or material to the first structure made of the first polymer to create raised structures or ribs;
b. mechanically linking the second structure made of the incompatible second polymer with the ribs or raised structures at the desired attachment point of the first and second structures by:
  b1. using heat shrinking or mechanical compression (such as crimping) to force the incompatible second polymer around the ribs or raised structures, or
  b2. in the case of raised structures formed as threads or nubs, attaching the second structure to the first structure by inter-engagement between the threads or nubs on the first structure and corresponding structures, such as internal threading, nub-receiving slots, or internal surfaces, of the second structure.

The option of using the welded raised structures as threads or nubs for a threaded, bayonet, pin-and-slot, snap-fit, or similar connection enables the second structure to be removed from the first structure and replaced whenever the second structure becomes worn during use. In addition, a threaded connection has the advantage of enabling axial adjustment of a distance or set back between the distal end of the protective tip and the distal end of the fiber, by rotating the protective tip.

In the illustrated embodiment, the first structure is an surgical laser fiber with an ETFE buffer layer, and the second structure is a protective structure to be attached to the ETFE buffer layer and made of an incompatible polymer such as, by way of example and not limitation, PTFE, PET, FEP or PFA.

BRIEF DESCRIPTION OF THE DRAWINGS

FIG. 1 is a side view of two structures made of incompatible polymers that have been joined by the method of the invention.

DETAILED DESCRIPTION OF THE PREFERRED EMBODIMENTS

Throughout the following description and drawings, like reference numbers/characters refer to like elements. It should be understood that, although specific exemplary embodiments are discussed herein there is no intent to limit the scope of present invention to such embodiments. To the contrary, it should be understood that the exemplary embodiments discussed herein are for illustrative purposes, and that modified and alternative embodiments may be implemented without departing from the scope of the present invention.

As illustrated in FIG. 1, a surgical laser fiber is stripped to expose a buffer layer 1 and a core or core/cladding section 5. A soft protective structure 3 having a generally cylindrical shape is to be attached to the end section of the buffer layer 1. The soft protective structure 3 may have a standoff structure of the type disclosed in PCT Publication No. WO 2017/192869 or Provisional Patent Appl. Ser. No. 62/648,108, in which the distal end of the protective structure extends beyond a tip of the fiber to serve as a standoff that prevents contact between the tip of the fiber and a stone during laser lithotripsy, although the principles of the invention are not limited to protective structures that extend beyond the tip of a fiber, but instead may include guiding structures, ferrules, or any other polymer structure intended to be attached to the fiber.

The buffer layer 1 is made of a first polymer such as ETFE, while the protective structure 3 is made of an incompatible polymer such as PTFE, PET, FEP or PFA. In order to attach the protective structure 3 to the buffer layer 1, bands of a material that is compatible with the material of the buffer layer 1, i.e., material that is compatible with ETFE in the illustrated example, is welded to the buffer layer 1 to form ribs, threads, or nubs 2. The material of the ribs, threads, or nubs 2 may be ETFE or another compatible material.

The protective tip 3 may then be secured to the buffer 1 by one of two methods. The first attachment method is to use mechanical compression, such as provided by a heat shrink or crimp sleeve 4 to force material of the protective tip 3 around the ribs, threads, or nubs 2.

The second attachment method is to utilize the welded-on bands as threads or nubs, and removably attach the protective tip 3 to the buffer layer 1 by pushing, twisting or turning in order to cause inter-engagement of internal threads, slots, or surfaces of the protective tip with the threads or nubs 2, resulting in a threaded, bayonet, push and twist, snap-fit, or similar removable connection or coupling between the protective tip and the optical fiber. In the case of a threaded connection, the protective tip may be also be rotated to adjust a distance or set back between the distal end of the protective tip and the distal end of the fiber.

What is claimed is:

1. A method of joining a first structure made of a first polymer to a second structure made of an incompatible second polymer, comprising the steps of:
   welding small bands of compatible tubing or material to the first structure to create raised structures or ribs; and
   mechanically linking the second structure made of the incompatible second polymer with the ribs or raised structures at a desired attachment point of the first and second structures.

2. The method of claim 1, wherein the step of mechanically linking the second structure with the ribs or raised structures comprises the step of using heat shrinking to force the incompatible second polymer around the ribs or raised structures.

3. The method of claim 1, wherein the step of mechanically linking the second structure with the ribs or raised structures comprises the step of using mechanical compression to force the incompatible second polymer around the ribs or raised structures.

4. The method of claim 1, wherein the ribs or raised structures form threads or nubs, and the step of mechanically linking the second structure with the ribs or raised structures comprising the step of attaching the second structure to the first structure by inter-engagement between the threads or nubs on the first structure and corresponding internal threading, nub-receiving slots, or surfaces of the second structure to form a threaded, bayonet, pin-and-slot, snap-fit, or otherwise removable connection.

5. The method of claim 1, wherein the first structure is an surgical laser fiber with an ETFE buffer layer, and the second structure is a protective structure to be attached to the ETFE buffer layer and made of an incompatible polymer.

6. The method of claim 1, wherein the incompatible polymer of the second structure is made of PTFE, PET, FEP or PFA.

7. The method of claim 1, wherein the first structure is made of ETFE and the second structure is made of PTFE, PET, FEP or PFA.

* * * * *